United States Patent
Wo et al.

(10) Patent No.: US 7,435,841 B2
(45) Date of Patent: Oct. 14, 2008

(54) PREPARATION OF HALOHYDROCARBYL PHOSPHONIC ACID DIESTERS

(75) Inventors: Shiming Wo, Monroe Township, NJ (US); John Marshall Baker, Charleston, SC (US)

(73) Assignee: Rhodia Inc., Cranbury, NJ (US)

( * ) Notice: Subject to any disclaimer, the term of this patent is extended or adjusted under 35 U.S.C. 154(b) by 376 days.

(21) Appl. No.: 11/075,127

(22) Filed: Mar. 8, 2005

(65) Prior Publication Data

US 2005/0203306 A1   Sep. 15, 2005

Related U.S. Application Data

(60) Provisional application No. 60/551,753, filed on Mar. 10, 2004.

(51) Int. Cl.
*C07F 9/02* (2006.01)
(52) U.S. Cl. ..................................................... 558/106
(58) Field of Classification Search .................. 558/106
See application file for complete search history.

(56) References Cited

U.S. PATENT DOCUMENTS

| | | | |
|---|---|---|---|
| 2,436,141 A | 2/1948 | Goebel | 260/461 |
| 2,899,454 A | 8/1959 | McBee et al. | 260/461 |
| 3,064,031 A | 11/1962 | Zimmerer | 260/461 |
| 3,242,236 A | 3/1966 | Moedritzer | 260/970 |
| 3,251,907 A | 5/1966 | Roy | 260/969 |
| 3,548,040 A | 12/1970 | Sorstokke et al. | 260/986 |
| 3,600,435 A | 8/1971 | Randall et al. | 260/502.4 P |
| 3,691,275 A | 9/1972 | Benghiat | 260/961 |
| 3,700,760 A | 10/1972 | Benghiat | 260/950 |
| 4,268,507 A | 5/1981 | Nguyen Mong | 424/217 |
| 4,338,440 A | 7/1982 | Hawkins | 544/110 |
| 4,483,705 A | 11/1984 | Purdum | 71/86 |
| 5,177,238 A | 1/1993 | Carter et al. | 558/125 |

FOREIGN PATENT DOCUMENTS

WO   WO 96/15134   * 11/1995

OTHER PUBLICATIONS

Ezquerra et al., Synthetic Communication, 1995, 25(2): 191-194.*
Gobel et al. (Phosphorus, Sulfur, and Silicon 1992) 73 (1-4), 67-80).
Ezquerra et al. (Synthetic Communications 1995) 25 (2), 191-4).
R. Washchbusch, et al. (Laboratoire Heteroelements et Coordination, URA CNRS 1499, DCPH, Ecole Polytechnique, Palaiseau, France, Comptes Rendus de L'Academie des Sciences, Series 11 C: Chimle (1998), 1(1),49-52).
Burton, D. J., Flynn, R. M., J. Fluorine Chemistry 10 (1977) 329.
Waschbush R., Carran J., and Savignac, P., Tetrahedron 52 (1996) 14199.
Ii, et al., Diethyl Iododifluoromethylphosphonate: A New Synthetic Method and its Reaction With Alkynes, Synthesis 1996, vol. 5, pp. 606-608.

* cited by examiner

*Primary Examiner*—Rei-tsang Shiao

(57) ABSTRACT

In a process for the production of halohydrocarbyl phosphonic acid diesters via a Michaelis-Arbuzov type reaction which results in high conversion and selectivity of product with ease of purification; the improvement comprises reacting hydrocarbyl halide with trihdydrocarbyl phosphite in a molar ratio of about 6:1 and in the presence of an effective amount of a polarity lowering additive.

20 Claims, No Drawings

PREPARATION OF HALOHYDROCARBYL PHOSPHONIC ACID DIESTERS

CROSS-REFERENCE TO RELATED APPLICATION

This application claims priority from U.S. Provisional Application Ser. No. 60/551,753 filed Mar. 10, 2004.

FIELD OF THE INVENTION

The present invention generally relates to an improved process for the production of diesters of halohydrocarbyl phosphonic acid that results in high yield and selectivity. More particularly, the present invention relates to a method of preparing haloalkyl phosphonates with exceptionally high yields, i.e., with minimum undesirable by-product formation via reactant ratio and reactive medium polarity control.

BACKGROUND OF THE INVENTION

Dihydrocarbyl hydrocarbyl phosphonates are a group of stable, organic phosphonic acid esters that are known to possess unique properties. These materials are neutral esters of phosphonic acids and tend to be clear, colorless, and mobile liquids. They are similar in many respects to the trihydrocaryl phosphates which have found a wide variety of commercial applications. The significant structural difference between the two is that the phosphonates have one hydrocarbyl radical attached directly to the phosphorous atom by a carbon-phosphorous bond. This structural difference gives the phosphonates several advantages over the phosphates, among these are higher flash points, greater thermal and hydrolytic stabilities, and different solubility characteristics.

Recently, halogenated versions of these phosphonates have been recognized as being extremely valuable intermediates for many commercially desirable products in the agricultural fields; e.g., products used in insecticidal, fungicidal, plant growth regulation, and bactericidal applications; as additives such as plasticizers in the polymer, resin and polymer fields; and ingredients in gasoline, lubrication, and fuel oil additive compositions. Most importantly, these halogenated phosphonates, especially highly purified compositions of these halogenated phosphonic acid diesters have been in great demand as starting materials for the synthesis of medicinal products, e.g., primarily as building blocks for pharmaceutical intermediates, and certain of these compounds have been known to possess remarkable medicinal activity in their own right, for example, as hypoglycemic and/or antiatherogenic agents (U.S. Pat. No. 4,268,507). These compounds provide an important means to introduce phosphonic moiety or moieties into active drugs.

The halogenated hydrocarbyl phosphonate esters to which the present invention is directed can be prepared by a number of synthetic methods known to those skilled in the art; however, the improved process discovery of this invention specifically relates to compounds prepared by the Michaelis-Arbuzov type reaction of phosphites with halogenated materials.

In 1992, Gobel et al. (Phosphorous, Sulfur and Silicon and Related Elements (1992), 73 (1-4), 67-80) while working to obtain diisopropyl bromomethylphosphonate for the synthesis of diphosphonylmethanes with different constituents on both phosphorous atoms via an Arbuzov type reaction scheme, reacted triisopropyl phosphite (0.25 moles) with methylene bromide (aka dibromomethane or DBM) (0.64 moles), i.e., a ratio of phosphite to DBM of 1:2.56 at from 145-150° C. and the reaction afforded yields of 48% diisopropyl bromomethylphosphonate together with 40% undesired tetraisopropyl methylenephosphonate after 47 hours. These results do not appear to be purified yields.

The reaction scheme of this reference is illustrated in (i) and (ii) below:

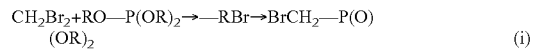

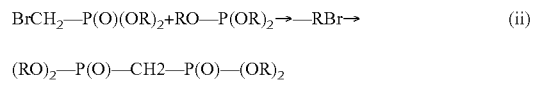

In 1995, Ezquerra et al. (Synthetic Communications (1995) 25(2), 191-4) published their activities relating to improving the Arbuzov type reaction yield of diethyl bromomethyl phosphonate also by removing the ethyl bromide by-product as it formed and by increasing the triethyl phosphite to dibromomethane reactant ratio to 1:4.

It was postulated that the primary reaction schemes are as depicted in (iii), (iv), and (v) below:

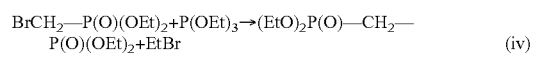

Ezquerra et al.'s approach was to increase the amount of dibromomethane relative to the triethylphosphite and to remove the ethyl bromide as it formed, and, in this manner, the by-product reaction schemes as depicted in (iv) and (v) would be minimized.

The reaction was conducted at about 100° C. for 48 hours while inert gas was gently bubbled through the reaction medium. After distillation of the liquid, diethyl bromomethyl phosphonate was obtained in a 40% yield.

Also illustrative of the present state of the art, in 1998, R. Waschbusch et al. [Laboratoire Heteroelements et Coordination, URA CNRS 1499, DCPH, Ecole Polytechnique, Palaiseau, France, Comptes Rendus de l'Academie des Sciences, Series 11c: Chimie (1998), 1(1), 49-52] published the results of a third study relating to activities seeking high yields and purity of diethyl dibromofluoromethyl phosphonate. In all these studies, a Michaelis-Arbuzov reaction between essentially equimolar quantities of triethyl phosphite and fluorotribromomethane, i.e., a 1:1 molar ratio, was used to form the phosphonate product.

The first study [Burton D. J., Flynn R. M., J. Fluorine Chem. 10 (1977) 329] was conducted at ambient temperatures in a diethyl ether solvent in the presence of light, suggesting a photo-catalyzed, i.e., a radical reaction mechanism; and reportedly resulted in low product yields. A second study [Waschbusch R., Carran J., Savignac P., Tetrahedron 52 (1996) 14199] reproduced the above-described process; failed to achieve acceptable yields; and switched to a hexane environment. This ambient temperature process realized better yields but required unacceptable reaction times of fourteen days.

The Waschbusch et al. group conducted the reaction also starting with a 1:1 molar ratio of the phosphite to the fluorotribromomethane in the presence of hexane. The reaction mixture was placed in a pressure bottle; sealed; and heated to 50° C. for 48 hours.

The reaction scheme is as depicted in (vi) below:

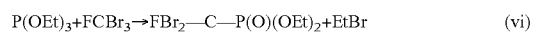

The hexane was evaporated on a rotary evaporator and the crude liquid distilled under reduced pressure to give 79-85% of the diethyl 1,1-dibromo-1-fluoromethylphosphonate product. The excellent product yield with low by-product impurities was realized by the Waschbusch et al. process primarily as a result of the reactivity of the fluorine atom. Because the Arbuzov reaction with fluorine is able to be carried out at such relatively low temperatures, the ethylene bromide by-product is unable to react with the phosphite starting material. Furthermore, the diethyl dibromofluoromethyl phosphonate is not as reactive as the starting $FCBr_3$, therefore it does not effectively react with the phosphite at this low temperature to give the diphosphonate by-product.

To date, the art has been unable to utilize Michaelis-Arbuzov reactions to produce high yields with commercially practicable purification means of dihydrocarbyl halohydrocarbyl phosphonates without using the fluorine atom and the attendant low temperature reactions as set forth in Waschbusch et al.

Accordingly, it is an object of this invention to provide a practical and efficient process for forming non-fluoro halohydrocarbyl phosphonic acid diesters in high selectivity and yield using controlled reaction conditions. It is also an object of this invention to provide an improved process for forming non-fluorohalohydrocarbyl phosphonic acid esters having increased purity.

Other objects will be evident from the ensuing description and appended claims.

SUMMARY OF THE INVENTION

The present invention is directed to a process which uses a combination of special parameters to unexpectedly provide a means of forming halohydrocarbyl phosphonic acid diesters in high conversion and selectivity via the Michaelis-Arbuzov type reaction of trihydrocarbyl phosphite with certain hydrocarbyl halides in the presence of a polarity lowering compound in the reaction mixture.

The improved process permits the production of halohydrocarbyl phosphonic acid diesters having increased purity by minimizing the contact between the product and the starting trihydrocarbyl phosphite and lowering the polarity of the reactive mixture thereby significantly decreasing the formation of undesirable side reaction products, which can not be easily removed from the desired product using conventional purification methods.

The present improved process requires reacting the trihydrocarbyl phosphite with a hydrocarbyl halide whereby the mole ratio of the hydrocarbyl halide to phosphite is greater than 2:1 and adding a low polarity compound to the reaction mixture to reduce the polarity of said mixture to below that of the hydrocarbyl halide.

DETAILED DESCRIPTION OF THE INVENTION

The present invention is an improved process for forming halohydrocarbyl phosphonic acid diesters by the reaction of a trihydrocarbyl phosphite with a hydrocarbyl halide in the presence of a polarity lowering compound. These phosphonic acid diesters are represented by the formula (vii) below:

in which

Z is halogen, haloalkyl or haloalkenyl,
wherein the alkyl or alkenyl in the haloalkyl group or the haloalkenyl group is from 1 to about 20 carbon atoms, and the halogen or the halogen moiety in the haloalkyl group or the haloalkenyl group has an atomic weight greater than 30;

X and Y are independently hydrogen, halogen, alkyl, alkenyl or aralkyl groups; the halogen has an atomic weight greater than 30; and the alkyl, or alkenyl, or aralkyl groups is from 1 to 20 carbon atoms; and R and $R_1$ are the same or different and are hydrocarbyl groups.

The process involves reacting the halide and phosphite reactants in a molar ratio of greater than 2:1 halide to phosphite, preferably 3:1 to 8:1, and most preferably in a ratio of about 6:1. Additionally, the polarity of the reaction mixture should be below that of the hydrocarbyl halide which is accomplished by the addition to said mixture at the beginning of the reaction of an effective amount of a polarity lowering compound.

Conventionally, halohydrocarbyl phosphonic acid diesters are synthesized using a Michaelis-Arbuzov type reaction by contacting a hydrocarbyl halide with an appropriate trihydrocarbyl phosphite compound. When the atomic weight of the halogen atom in the Arbuzov halide is greater than 30, i.e., the halide is a chloride, bromide, or iodide, elevated temperatures are necessary to activate the reaction, i.e., temperatures of from about 80° C. to about 160° C. At these temperature conditions, the desired halohydrocarbyl phosphonic acid diester product will further react with the phosphite reactant which will lead to the formation of undesirable diphosphonates. In order to suppress this by-product reaction, a large excess of the hydrocarbyl halide is usually used. However, this approach, which effectively reduces the formation of the diphosphonates by-product, unavoidably leads to the formation of complex reaction mixtures which are formed in the polar reaction medium that exists in the presence of the product, phosphite reactant, and excess hydrocarbyl halide mixtures.

The following reactions, depicted by using an initial Arbuzov reaction of triisopropyl phosphite with dibromomethane to yield a bromomethyl phosphonate product, are illustrative of the undesirable, complex by-product side reactions that can occur when a large excess of the dibromomethane reactant is used to minimize the diphosphonates by-product formation. As the reaction proceeds, the concentration of the bromomethyl phosphonate will increase. Since the reaction mixture is relatively polar due to the large excess of dibromomethane, side reactions start to occur such as those indicated below in (viii) and (ix):

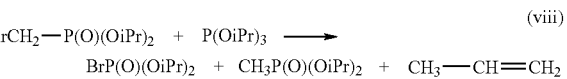

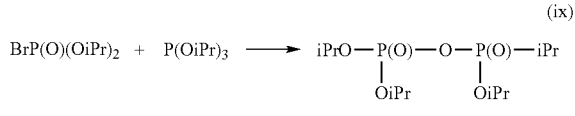

(ix)

(x)

In reaction pathway (viii), the triisopropyl phosphite attacks the bromine atom of the bromomethylphosphonate product to give diisopropyl bromophosphate and diisopropyl methylphosphonate. The diisopropyl bromo phosphate is very active and can react with the original phosphite reactant to give complex mixtures such as the phosphate-phosphonate compounds as depicted in reaction pathway (ix). Furthermore, some of the impurities formed by these side reactions are thermally unstable and can undergo uncontrollable decomposition reactions during distillation.

For example, in an attempt to synthesize diisopropyl bromomethyl phosphonate by the Michaelis-Arbuzov reaction sequence illustrated above, i.e., by reacting triisopropyl phosphite and dibromomethane in a molar ratio of 1:4, a complex reaction mixture containing about 50% of the desired compound was obtained. The reaction product could not be effectively purified by wiped film evaporation technique due to the complexity of the mixture. Conventional fractional distillation of the reaction mixture led to the formation of a large amount of fumes which is indicative of decomposition. Thus, the suppression of the diphosphonate by-product inevitably complicates the purification of the halohydrocarbyl phosphonate product and results in a process that is unsuitable for industrial application.

The instant invention relates to the surprising discovery that the formation of the undesirable impurities largely depends upon the polarity of the reaction system. Thus, it has been discovered that, to minimize the formation of the impurities, especially under conditions wherein formation of the diphosphonate is being suppressed via the use of high hydrocarbyl halide to phosphite ratios, an additive or combination of additives that can effectively reduce the polarity of the reaction medium should be employed.

The polarity lowering additives that can be used in this invention are chemically stable under the conditions of the reaction, i. e., non-reactive with the other components in the reaction mixture, and possess a polarity lower than that exhibited by the hydrocarbyl halide.

Examples of the polarity lowering additives useful in the present invention include, but are not limited to the following:

(a) aromatic hydrocarbons such as benzene, toluene, and xylene;

(b) alkanes, alkenes, alkynes, cycloalkanes, and cycloalkenes such as pentane, hexane, heptane, octane, and their isomers; and (c) other inert organic compounds such as phosphonates, hydrogen phosphites, and phosphates.

The effective amount of the polarity lowering additive can vary depending on the degree of suppression of the complex impurities production desired. The higher the amount of the additive used, the less amount of the undesirable impurities are formed. The determination of the correct amount to be used in a given situation is well within the purview of those skilled in the art.

Trihydrocarbyl phosphite compounds which are useful as reactants in the process of this invention are of the following general formula (x):

in which R, $R_1$ and $R_2$ are the same or different and are hydrocarbyl groups.

By the term hydrocarbyl is meant hydrocarbon groups such as the aliphatic and aromatic groups. The hydrocarbon groups may be substituted by or include only such groups as do not affect the essential reactivity or character of the group. Such groups include any inert or non-reactive substituent such as chloro groups, bromo groups, nitro groups, hydroxy groups, mercapto groups, sulfone groups, alkoxy groups, aryloxy groups, nitrile, thioether groups, ether groups, ester groups, keto groups, and the like.

Illustrative of the aliphatic groups that are represented by R, $R_1$, and $R_2$ above are the alkyl groups and their cyclic isomers. Illustrative of the aromatics are benzyl, phenylethyl, naphthylmethyl, naphthylethyl, and the like.

Preferred are when R, $R_1$, and $R_2$ are the same or different and are alkyl having from 1 to about 20 carbon atoms or cycloalkyl having from 3 to about 20 carbon atoms. Illustrative of these preferred R, $R_1$, and $R_2$ substituents are alkyls, such as methyl, ethyl, propyl, isopropyl, n-butyl, sec-butyl, pentyl and its isomers, hexyl and its isomers, heptyl and its isomers, and the like; and cycloalkyl such as, cyclopropyl, cyclobutyl, cyclopentyl, cyclohexyl, and the like.

The preferred R, $R_1$, and $R_2$ substituents may be substituted with one or more functional groups which are relatively non-reactive with the reactants, products, and additives employed in the process under process conditions. Illustrative of such non-reactive functional groups are phenyl, chloro, bromo, alkoxy, aryloxy, alkylthio, arylthio, alkylalkoxy, (e.g., methyl methoxy, methyl ethoxy, and methyl propoxy), cyano, carboxy, alkoxycarbonyl, perfluoroalkyl (e.g., trifluoromethyl) and the like.

The more preferred phosphite compound for use in the practice of this invention are those in which R, $R_1$, and $R_2$ are the same and are alkyl having from 1 to about 4 carbon atoms. Among these most preferred embodiments are the particularly most preferred embodiments in which R, $R_1$, and $R_2$ are the same and are methyl, ethyl, or isopropyl.

Phosphite compounds which can be used in the practice of this invention can be obtained from commercial sources or prepared in accordance with conventional procedures. For example, useful phosphite compounds can be obtained by reacting phosphorous trichloride with three equivalents of the corresponding alcohol in the presence of a base such as triethylamine in a suitable solvent as described in greater detail in "Organophosphorous Pesticides: Organic and Biological Chemistry" by Morhusa Eto, p 19; CRC Press Inc. (1079) and "Organic Phosphorous Compounds" (Vol. 5) by G. M. Kosolappoff and L. Maier (Wiley-Interscience, 1973) at pp. 32-37.

The hydrocarbyl halide compounds which are useful as reactants in the process of this invention are of the general formula (xi):

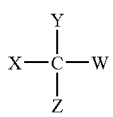

wherein

W is a halogen having an atomic weight greater than 30, such as chlorine, bromine and iodine;

Z is halogen, haloalkyl, haloalkenyl, or haloaralkyl wherein the alkyl, alkenyl or aralkyl group in the haloalkyl, haloalkenyl, or haloaralkyl group respectively is from 1 to about 20 carbon atoms; preferably from 1 to about 12 carbon atoms; and the halogen or the halo group in the haloalkyl, haloalkenyl, or haloaralkyl group has an atomic weight greater than 30, such as chlorine, bromine, and iodine; wherein the preferred choice for Z is chlorine, bromine, or iodine;

X and Y are independently hydrogen, halogen, alkyl, alkenyl, or aralkyl groups; and the halogen has an atomic weight greater than 30, such as chlorine, bromine and iodine; and the alkyl, alkenyl, or aralkyl groups is from 1 to 20 carbon atoms. The alkyl, alkenyl, or aralkyl groups may be substituted by or include only such groups as do not affect the essential reactivity or character of the group. Such groups include any inert or non-reactive substituent such as chloro groups, bromo groups, nitro groups, hydroxy groups, mercapto groups, sulfone groups, alkoxy groups, aryloxy groups, nitrile, thioether groups, ether groups, ester groups, keto groups, and the like.

Illustrative of the alkyl, alkenyl, and aralkyl groups are the isomers of acyclic and cyclic isomers of alkyls and alkenes, benzyl, phenylethyl, naphthylmethyl, naphthylethyl, and the like.

The preferred alkyl, alkenyl, and aralkyl groups are the alkyl groups having from 1 to about 20 carbon atoms or the cycloalkyl groups having from 3 to about 20 carbon atoms. Illustrative of these preferred substituents are alkyls, such as methyl, ethyl, propyl, isopropyl, n-butyl, sec-butyl, pentyl and its isomers, hexyl and its isomers, heptyl and its isomers, and the like; and cycloalkyls, such as cyclobutyl, cyclopropyl, cyclohexyl, cyclopentyl, and the like.

The preferred substituents for X and Y may be substituted with one or more functional groups which are relatively non-reactive with the reactants, products, and additives employed in the process under process conditions. Illustrative of such non-reactive functional groups are chloro, bromo, alkoxy, aryloxy, alkylthio, arylthio, alkylalkoxy, (e.g., methyl methoxy, methyl ethoxy, and methyl propoxy), cyano, carboxy, alkoxycarbonyl, perfluoroalkyl (e.g., trifluoromethyl) and the like.

The more preferred hydrocarbyl group in the hydrocarbyl halide compound is an alkyl group having from 1 to about 12 carbon atoms. The most preferred hydrocarbyl group in the hydrocarbyl halide compound is hydrogen or an alkyl group having from 1 to about 4 carbon atoms. Among these most preferred embodiments are hydrogen, methyl, ethyl and isopropyl.

Illustrative of the halohydrocarbyl compounds are tetrachloromethane, chloroform, dichloromethane, tetrabromomethane, tribromomethane, dibromomethane, bromotrichloromethane, dibromodichloromethane, diiodomethane, 1,1-dichloroethane, 1,1,1-trichloroethane, 1,1-dibromoethane, 1,1,1-tribromoethane, 1,2-dichloroethane, 1,2-trichloroethane, 1,1,2,2-tetrachloroethane, 1,2-dibromoethane, 1,1,2-tribromoethane, 1,1,2,2-tetrachloroethane, 1,2-dibromobutane, 1,3-dibromopropane, 1,4-dibromobutane, 1,5-dibromopentane, 1,6-dibromohexane, 1,12-dibromododecane, 1-bromo-2-chloroethane, and 1-bromo-2-iodoethane.

The preferred halohydrocarbyl compounds are dibromomethane, bromochloromethane, diiodomethane, tribromomethane, trichloromethane, dibromochloromethane, dibromodichloromethane, tribromochloromethane, tetrabromomethane, and tetrachloromethane. The more preferred is dibromomethane.

The halohydrocarbyl compounds which can be used in the practice of this invention can be obtained from commercial sources or prepared in accordance with conventional procedures.

The temperature employed in the process of this invention can be varied widely depending on factors known to those skilled in the art. Reaction will generally be carried out at a temperature greater than about 80° C. Temperatures within the range of from about 80° C. to about 160° C. are preferred and reaction temperatures of from about 80° C. to about 140° C. are particularly preferred. In the most preferred embodiments of the invention, the reaction is conducted at a temperature of about 100° C. to about 130° C.

The reaction may be carried out at atmospheric pressure or above atmospheric pressure in a sealed vessel. For convenience, and to ease removal of certain by-products during the reaction if so desired, the reaction is preferably carried out above atmospheric pressure.

The process of this invention is conducted for a period of time sufficient to produce the desired compound in adequate yield. Reaction times are influenced to a significant degree by the reaction temperature; the concentration and choice of reactants; the choice and concentration of the polarity lowering additive; and other factors known to those skilled in the art. In general, reaction times can vary from a few hours to several days or longer.

The halohydrocarbyl phosphonic acid diester product can be isolated from the reaction mixture and purified by well known, art recognized techniques such as fractional distillation, the wipe film evaporation, and/or conventional washing techniques.

Excess halohydrocarbyls and the polarity lowering additives can be recycled.

The process of this invention can be conducted in a batch, semi-continuous or continuous fashion. The reaction can be conducted in a single reaction zone or in a plurality of reaction zones, in series or in parallel; or it may be conducted intermittently or continuously in an elongated tubular zone or series of such zones. The materials of construction employed should be inert to the reactants during the reaction and the equipment should be fabricated such that it is able to withstand the reaction temperatures and pressures.

The invention will now be described with reference to a number of specific examples which are to be regarded solely as illustrative of the methods and compositions of this invention and not as restrictive of the scope thereof.

EXAMPLE I

Comparative Example IA

To synthesize diisopropyl bromomethylphosphonate (DIPBMP), a two-necked 500 mL round bottom flask, was equipped with a 2 section Snyder distilling column and a distilling head. A 1.42 moles of dibromomethane (DBM) (248 g) and then 0.36 moles of triisopropyl phosphite (75 g)

was added (TiPP) to the flask and the resulting mixture was degassed by bubbling nitrogen into the solution for 10 minutes. The mixture was then heated to a set point T of 110° C. The mixture was allowed to react for 25 hours over a four day period with the T of the mass between 105-109° C.

The completed reaction mixture had the composition identified in Table I below based on gas chromatographic (GC) area integration. The mixture contained 49.5% of the diisopropyl bromomethylphosphonate and 17.3% impurities which could not be removed effectively. After a repeated careful distillation via wiped film evaporation technique, DIPBMP with 86% purity was isolated with only 20% overall yield based on the TiPP reactant.

Example IB

A reaction was carried out using the same molar ratio of TiPP to DBM as in Example IA; however, 1.92 moles of a polarity lowering additive, namely xylene was initially added to the flask together with the DBM reactant and the phosphite.

A Buchi 150 psi/1.5 L autoclave reactor was flushed with nitrogen and the jacket temperature was set to 50° C. In a 1 L Erlenmeyer flask, triisopropyl phosphite (260 g, 1.25 moles), dibromomethane (869 g, 5.0 moles), and xylene (isomers plus ethylbenzene, 204 g, 1.92 moles) were combined giving a total volume of 900 mL. Using a liquid pump, the autoclave was charged with the reaction mixture. The system was pressurized with nitrogen to 20 psig and then depressurized. This procedure was repeated three more times.

The autoclave was sealed and heated to a set reaction T of 125° C. with stirring at 400 rpm. The reaction was continued at 125° C. for 24 hours with the pressure steadily increasing to 24 psig. After 24 hours at 125° C., the reaction afforded a mixture with components as identified in Table I having 63% of the DIPBMP product and only 1.9% of the unknown impurities based on GC area integration.

TABLE I

| Components | W/O Polarity Lowering Additive (Xylene) % Example 1A | W Polarity Lowering Additive (Xylene) % Example 1B |
| --- | --- | --- |
| Diisopropyl bromomethyl phosphonate (DIPBMP) | 49.5 | 63.1 |
| Tetraisopropyl methylene diphosphonate | 7.2 | 14.1 |
| Triisopropyl phosphite (unreacted) (TiPP) | 7.3 | 5.2 |
| Triisopropyl phosphate | 3.3 | 2.5 |
| Diisopropyl hydrogen phosphonate | 0.0 | 7.1 |
| Diisopropyl methyl phosphonate | 8.6 | 2.7 |
| Diisopropyl isopropyl phosphonate | 0.0 | 2.3 |
| Unknown Impurities | 17.3 | 1.9 |

Comparative Example II

A reaction was carried out as in Example IA under essentially the same reaction conditions with the same reactants; however 124 g of the polar solvent propionitrile was initially added to the flask together with the 1.42 moles of the DBM reactant. After 0.36 moles of TiPP was added to the flask, the mixture was given a 10 minute nitrogen degassing; allowed to heat to a 110° C. set point, and to react for 21.5 hours over a 3 day period with mass T of 98° C. Table II depicts the composition percentages based on GC area integration results.

TABLE II

| Components | Percentage (%) |
| --- | --- |
| Diisopropyl bromomethylphosphonate (DIPBMP) | 9.7 |
| Tetraisopropyl methylenediphosphonate | 0.4 |
| Triisopropyl phosphite, unreacted (TiPP) | 43.5 |
| Triisopropyl phosphate | 2.9 |
| Diisopropyl methylphosphonate | 8.6 |
| Unknown phosphate-phosphonate Impurities | 27.0 |

It is to be noted that even though only slightly more than half of the phosphite reactant actually reacted, nearly one-half of the reacted TiPP ended up as unknown impurities and only 9.7% of DIPBMP product was produced.

EXAMPLE III

A reaction was carried out as in Example IB under essentially the same reaction conditions with the same apparatus, and the same reactants and polarity lowering additive; however, the molar ratio of the reactant and additive components were as follows: TiPP to DBM to xylene: 1/5.7/2.2 respectively. The completed reaction mixture resulted in 69.5% DIPBMP product. The excess dibromomethane reactant and xylene were removed via distillation and the stripped reaction mixture was subsequently washed with 3 parts of xylene and 4 parts of 0.1 N NaOH. The aqueous layer was removed and the organic layer washed with 4 parts of water three times. The xylene was removed from the washed sample which afforded diisopropyl bromomethylphosphonate product with 87% purity in a yield of 50% based on the initial TiPP reactant.

EXAMPLE IV

The Buchi autoclave reactor and associated circulator was flushed with nitrogen and heated as in Example IB. In a 1 L Erlenmeyer flask, triisopropyl phosphite (229 g, 1.11 moles), dibromoethane (109 g, 6.29 moles), and toluene (258 g, 2.8 moles) were combined. Using a fluid pump, the autoclave was charged with the reaction mixture. The system was pressurized with nitrogen to 20 psig and then depressurized, and this procedure was repeated three more times.

The autoclave was sealed and heated to a set reaction temperature T of 120° C. with stirring at 400 rpm. The mixture was allowed to react for 24 hours with the pressure steadily increasing to 29 psig. After the mixture was cooled to room temperature, 1530.1 g was transferred to a 1 L reactor which was equipped with a distilling column. Under nitrogen, the mixture was heated and the volatiles were removed at temperatures between about 100 to 140° C. under reduced pressure (maximum vacuum of 26 mm Hg). A total of 1185 g of distillate was collected. The crude product was allowed to cool to room temperature and a 491.4 g portion of toluene was added (approximately a 3 to 1 dilution) followed by the addition of a 754.0 g solution of 1.2% NaOH.

The mixture was stirred at 200 rpm for 30 minutes. The two phases were allowed to separate and settle. The two distinct layers formed within one minute. The bottom aqueous layer (770.1 g) was removed and the organic layer was washed with 750 g of water four times.

The organic layer was separated and the toluene was removed under reduced pressure, which afforded 141.4 g of the diisopropyl bromomethylphosphonate product with 50% yield based on the triisopropyl phosphite reactant. Table III depicts the composition percentages of the crude reaction mixture before the washing procedure and the final composition percentage after washing.

TABLE III

| Components | Crude Mixture Before Wash (%) | Final Mixture After Wash (%) |
|---|---|---|
| Diisopropyl bromomethyl phosphonate (DIPBMP) | 71 | 86.2 |
| Tetraisopropyl methylene diphosphonate | 9.6 | 3.2 |
| Triisopropyl phosphite, unreacted (TiPP) | 1.2 | 3.2 |
| Triisopropyl phosphate | 2.9 | 3.9 |
| Diisopropyl methyl phosphonate | 3.3 | 0.5 |
| Diisopropyl isopropyl methyl phosphonate | 1.4 | 1.6 |
| Diisopropyl hydrogen phosphite | 4.2 | 0.8 |
| Unknown Phosphate-phosphonate Impurities | 4.3 | 2.8 |

It can readily be seen that one of the key advantages of the unique process of this invention is that there is a minimum formation of the unidentified impurities and the diphosphonates that can not be removed from the desired halohydrocarbyl phosphonic acid diester product very effectively or safely by conventional purification methods such as distillation, washing or wiped film evaporation. In fact, the synthesis method of the present invention is so efficient that the halohydrocarbyl phosphonic acid diester product can be obtained with a purity exceeding 75%, and usually above 85%, by a simple, aqueous wash.

Although this invention has been described in detail with particular reference to preferred embodiments thereof, it will be understood that variations and modifications can be effected within the spirit and scope of this invention as described hereinabove and as defined in the appended claims.

The invention claimed is:

1. A process for producing halohydocarbyl phosphonic acid diesters of the formula (I):

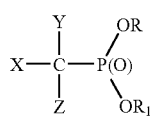

in which
Z is halogen;
X and Y are hydrogen;
the halogen has an atomic weight greater than 30; and
R and $R_1$ are the same or different and are hydrocarbyl groups;
which process comprises reacting a trihydrocarbyl phosphite of the formula (II):

in which
R and $R_1$ are the same or different and have the meanings given under formula (I);
$R_2$ has the same meaning as R and $R_1$ given under formula (I) and is the same or different from either R or $R_1$;
with a hydrocarbyl halide of the formula (III):

in which
Z, X and Y have the meaning given in formula (I), and
W is a halogen having an atomic weight greater than 30;
in the presence of an effective amount of a polarity lowering additive selected from the group consisting of benzene, toluene, xylene, and alkane, the alkane selected from the group consisting of pentane, hexane, heptane, octane, and their isomers;
wherein
the molar ratio of the hydrocarbyl halide reactant to the trihydrocarbyl phosphite reactant is greater than from 2:1.

2. The process of claim 1 wherein the polarity lowering additive is selected from the group consisting of xylene, toluene, hexane, and heptane.

3. The process of claim 1 wherein
R, $R_1$ and $R_2$ are isopropyl;
the polarity lowering additive is xylene or toluene; and
the molar ratio of the halide reactant to phosphite is about 6:1.

4. The process of claim 3 wherein
Z is bromine;
W is bromine; and
R, $R_1$, and $R_2$ are isopropyl.

5. The process of claim 1 wherein the process comprises, subsequent to the reacting step, the additional step of aqueous washing the halohydrocarbyl phosphonic acid diester product to obtain a product purity level above 75% based on the trihydrocarbyl phosphite reactant; and isolating the purified product.

6. The process of claim 5 wherein the washing step comprises washing the halohydrocarbyl phosphonic acid diester product in an aqueous wash comprising water, aqueous base solutions, or aqueous acid solutions.

7. The process of claim 6 wherein the aqueous base solution is an aqueous sodium hydroxide solution or an aqueous sodium carbonate solution.

8. The process of claim 6 wherein the aqueous acid solution is an aqueous hydrochloric acid solution or an aqueous sulfuric acid solution.

9. The process of claim 5 wherein the aqueous washing is conducted at ambient temperatures or higher to increase the efficiency of the washing step.

10. The process of claim 5 wherein subsequent to the washing step, stripping is conducted on the washed product.

11. The process of claim 5 wherein prior to the washing step, the step of removing volatiles is conducted; and subsequently, the step of adding organic solvents is performed.

12. The process of claim 11 wherein the organic solvent is selected from the group consisting of heptane, hexane, toluene, and xylene.

13. The process of claim 11 wherein the washing step comprises washing the halohydrocarbyl phosphonic acid diester product in an aqueous wash comprising water, aqueous base solutions, or aqueous acid solutions.

14. The process of claim 13 wherein the aqueous base solution is an aqueous sodium hydroxide solution or an aqueous sodium carbonate solution.

15. The process of claim 13 wherein the aqueous acid solution is an aqueous hydrochloric acid solution or an aqueous sulfuric acid solution.

16. The process of claim 13 wherein the aqueous washing is conducted at ambient temperatures or higher to increase the efficiency of the washing step.

17. The process of claim 13 wherein subsequent to the washing step, stripping is conducted on the washed product.

18. The process of claim 10 wherein the polarity lowering additive and the excess halohydrocarbon recovered is recycled.

19. The process of claim 11 wherein the polarity lowering additive and the excess halocydrocarbon recovered is recycled.

20. The process of claim 17 wherein the organic solvent removed is recycled.

\* \* \* \* \*